United States Patent [19]

Dao-cong et al.

[11] Patent Number: 5,527,764
[45] Date of Patent: Jun. 18, 1996

[54] 3-ARYLTHIONOURACILS USEFUL AS HERBICIDES, DEFOLIANTS, AND DESICCANTS

[75] Inventors: Dong Dao-cong, Guelph, Canada; Alan W. Dalrymple, Lindale, Tex.

[73] Assignees: Uniroyal Chemical Company, Inc., Middleburt, Conn.; Uniroyal Chemical Ltd./Ltee, Elmira, Canada

[21] Appl. No.: 306,345

[22] Filed: Sep. 15, 1994

[51] Int. Cl.⁶ .......................... C07D 239/54; A01N 43/54
[52] U.S. Cl. .......................... 504/243; 544/309; 544/314; 504/168; 504/178; 504/116
[58] Field of Search ..................... 504/243, 116, 504/178, 168; 544/309, 314

[56] References Cited

U.S. PATENT DOCUMENTS

| | | | |
|---|---|---|---|
| 4,746,352 | 5/1988 | Wenger | 71/90 |
| 4,812,164 | 3/1989 | Wenger | 71/92 |
| 4,943,309 | 7/1990 | Bell | 71/74 |
| 4,981,508 | 1/1991 | Strunk | 71/92 |
| 5,176,735 | 1/1993 | Bell | 504/168 |

FOREIGN PATENT DOCUMENTS

| | | |
|---|---|---|
| 0195346 | 9/1986 | European Pat. Off. . |
| 0396250 | 11/1990 | European Pat. Off. . |
| 0438209 | 7/1991 | European Pat. Off. . |
| 91/07392 | 5/1991 | WIPO . |

*Primary Examiner*—John M. Ford
*Attorney, Agent, or Firm*—Daniel Reitenbach

[57] ABSTRACT

Compounds having the structural formula

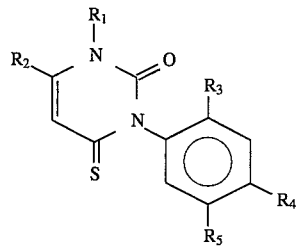

wherein $R_1$ is $C_1-C_4$ alkyl, $R_2$ is $C_1-C_4$ alkyl or haloalkyl, $R_3$ and $R_4$ are hydrogen or halogen, and $R_5$ is hydrogen or $COOR_6$ wherein $R_6$ is $C_1-C_8$ linear or branched alkyl, alkenyl, or alkynyl, and compositions comprising the compounds. The compounds and compositions are useful as herbicides, desiccants and defoliants.

28 Claims, No Drawings

3-ARYLTHIONOURACILS USEFUL AS HERBICIDES, DEFOLIANTS, AND DESICCANTS

FIELD OF THE INVENTION

The present invention is related to novel aryl-substituted thionouracils. More particularly, the present invention is related to novel arylthionouracils useful as pre- and post-emergent herbicides and plant growth regulant compounds.

BACKGROUND OF THE INVENTION

The control of weeds and other undesirable plants is important because weeds and other undesirable plants undermine the production of useful agricultural crops by inhibiting the production of foliage, fruit or seeds of these useful plants. The control of weeds on noncropped areas is also essential because, for example, weeds present a potential fire hazard and can give off allergy-aggravating pollen.

Plant growth regulation is also of economic importance, particularly in the area of harvest aid. The field of harvest aid utilization includes the defoliation of the crop plant; the desiccation of its leaves, stems, and other aerial organs; the control of late-season regrowth (e.g., for cotton); the promotion or inhibition of fruit or flower abscission; the concentration of crop maturity; and the enhancement of consumer-preferred quality factors.

Under normal conditions, many crop plants do not mature uniformly or in a timely fashion that would facilitate an efficient and optimum harvest, either due to equipment scheduling or weather considerations. Crops such as cotton, potato, sunflower, and seed legumes require either desiccation or defoliation before harvest can be effectively accomplished. For example, when cotton is not defoliated the leaves can interfere with mechanized picking apparatus which are frequently employed. Also, leaves can contaminate the cotton lint with trash or green stain, which reduces the quality of the fiber or reduces the efficiency of the ginning process. Likewise, potato vines need to be desiccated for efficient mechanical digging. In addition, upon desiccation of potato leaves and stems, the tuber skin matures and becomes less susceptible to damage from the digger and postharvest handling. Seed legumes and sunflowers are also mechanically harvested, and this process is facilitated if the leaves and stems are removed or desiccated. As with cotton and potato, such defoliation or desiccation also ripens the seed uniformly, accelerates the rate of seed maturation, and conditions the pod or head for easy harvest. In addition, the mechanical harvest of many fruit species, such as citrus, grape and olive, is routinely facilitated by the application of chemical abscission-inducing agents.

U.S. Pat. No. 4,746,352 describes certain 3-(5-carboxy-4-substituted-phenyl)-(thio)uracil esters useful for controlling weeds.

U.S. Pat. No. 4,812,164 describes certain ethers of 3-aryluracils useful as herbicides.

U.S. Pat. No. 4,943,309 describes a method for regulating the growth of plants using certain 3-carbonylphenyl uracil compounds.

U.S. Pat. No. 4,981,508 describes 1,4-benzoxazin-3-one substituted uracils useful as herbicides.

U.S. Pat. No. 5,176,735 describes a method for desiccating plants using certain 3-carbonylphenyl uracil compounds.

EP 0 438 209 A1 describes certain uracil derivatives useful as pesticides.

It is an object of this invention to provide novel aryl-substituted thionouracil derivatives for use in controlling weeds and other undesirable plants, and for use as desiccants and defoliants.

It is also an object of this invention to provide novel herbicidal, desiccant and defoliant compositions comprising the novel aryl-substituted thionouracil derivatives.

Additionally, it is a further object of this invention to provide a method for controlling undesirable plants using the novel aryl-substituted thionouracil derivatives.

It is a further object of this invention to provide a method for desiccating plants using the novel aryl-substituted thionouracil derivatives.

Finally, it is an object of this invention to provide a method for defoliating plants using the novel aryl-substituted thionouracil derivatives.

DESCRIPTION OF THE INVENTION

This invention relates to a compound of the formula

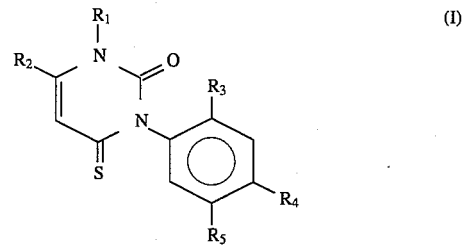

wherein $R_1$ is $C_1$–$C_4$ alkyl, $R_2$ is $C_1$–$C_4$ alkyl or haloalkyl, $R_3$ and $R_4$ are hydrogen or halogen, and $R_5$ is hydrogen or $COOR_6$ wherein $R_6$ is $C_1$–$C_8$ linear or branched alkyl, alkenyl, or alkynyl.

Preferably, $R_2$ is $C_1$–$C_4$ fluoroalkyl;

More preferably, $R_1$ is methyl, $R_2$ is trifluoromethyl, $R_3$ is halogen or hydrogen, $R_4$ is halogen, and $R_5$ is hydrogen or $COOR_6$ wherein $R_6$ is a $C_1$–$C_4$ alkyl group.

Still more preferably, $R_1$ is methyl, $R_2$ is trifluoromethyl, $R_3$ is fluorine, chlorine or hydrogen, $R_4$ is chlorine or fluorine, and $R_5$ is hydrogen or $COOR_6$ wherein $R_6$ is isopropyl or cyclopropyl.

Most preferably, $R_1$ is methyl, $R_2$ is trifluoromethyl, $R_3$ is fluorine or hydrogen, $R_4$ is chlorine, and $R_5$ is hydrogen or $COOR_6$ wherein $R_6$ is isopropyl or cyclopropyl.

This invention also relates to an agriculturally useful composition. This composition, having utility as a herbicide, desiccant or defoliant, comprises the compound of formula I above and a suitable carrier therefor.

Preferably, the composition of the present invention comprises the compound of formula I wherein $R_2$ is $C_1$–$C_4$ fluoroalkyl.

More preferably, the composition of the present invention comprises the compound of formula I wherein $R_1$ is methyl, $R_2$ is trifluoromethyl, $R_3$ is halogen or hydrogen, $R_4$ is halogen, and $R_5$ is hydrogen or $COOR_6$ wherein $R_6$ is a $C_1$–$C_4$ alkyl group, and a suitable carrier therefor.

Still more preferably, the composition of the present invention comprises the compound of formula I wherein $R_1$ is methyl, $R_2$ is trifluoromethyl, $R_3$ is fluorine, chlorine or hydrogen, $R_4$ is fluorine or chlorine, and $R_5$ is hydrogen or $COOR_6$ wherein $R_6$ is isopropyl or cyclopropyl, and a suitable carrier therefor.

Most preferably, the composition of the present invention comprises the compound of formula I wherein $R_1$ is methyl, $R_2$ is trifluoromethyl, $R_3$ is fluorine or hydrogen, $R_4$ is chlorine, and $R_5$ is hydrogen or $COOR_6$ wherein $R_6$ is isopropyl or cyclopropyl, and a suitable carrier therefor.

The composition of the present application is useful as a herbicidal, desiccant, or defoliating composition. Accordingly, the concentration of the compound of formula I in the composition of this invention useful as an herbicide is an herbicidally effective amount of the compound. Similarly, the concentration of the compound of formula I in the composition of this invention useful as a desiccant is a desiccatingly effective amount of the compound. And finally, the concentration of the compound of formula I in the composition of this invention useful as a defoliant is a defoliatingly effective amount of the compound.

As stated above, the composition of the present invention comprises, as one component thereof, a carrier suitable for admixture with the compound of formula I. The carrier can be any carrier material known in the art which does not have a deleterious effect on the activity of the compound of formula I, such as, finely-divided particulate solids, granules, pellets, wettable powders, flowable liquids, soluble powders, aqueous or organic solvents, aqueous or organic dispersants or aqueous or organic emulsifying agents.

Among the materials that can be utilized to produce a solid carrier, that is, a carrier in the form of finely-divided particulates, granules, pellets, wettable powders, soluble powders and the like, are such organic and inorganic materials as attapulgite clay, sand, vermiculite, corn cob, activated carbon and mineral silicates. Useful mineral silicates include mica, talc, pyrophyllite clays, and the like.

A solid composition can be prepared with the compound of formula I impregnated onto the solid carrier. Alternatively, the compound can be formulated into a wettable powder by grinding it into a fine powder and mixing it with the solid carrier to which a surface active dispersing agent has been added. The wettable powder is then dispersed in water and sprayed onto the soil surface, the crop to be protected, and/or the weeds.

The composition of this invention can be a liquid composition, such as a liquid solution or liquid emulsion. In a liquid solution, the compound of formula I is dissolved in an aqueous or organic solvent. Preferred solvents include aromatic or aliphatic hydrocarbons. Of the hydrocarbons, toluene is particularly preferred.

Preferably, the liquid composition is an emulsion. The compound of formula I can be dissolved in an organic solvent to which a surface active dispersing agent is added. Water is then added to form the emulsion. The water emulsion can then applied to the locus to be protected, usually by spraying. Alternatively, the emulsion can utilize an organic liquid, such as oil, as the dispersant.

The surface active dispersing agent can be any of those known in the art. Examples of appropriate surface active agents can be found in McCutcheron's Detergents and Emulsifiers, Allured Publishing Company, Wedgewood, N.J. (1980).

The present invention also relates to a method for controlling undesired vegetation, which comprises applying an effective amount of the compound of formula I to the locus to be protected.

Preferably, the method of the present invention for controlling undesired vegetation comprises applying an effective amount of the compound of formula I wherein $R_2$ is $C_1$–$C_4$ fluoroalkyl.

More preferably, the method of the present invention for controlling undesired vegetation comprises applying an effective amount of the compound of formula I wherein $R_1$ is methyl, $R_2$ is trifluoromethyl, $R_3$ is halogen or hydrogen, $R_4$ is halogen, and $R_5$ is hydrogen or $COOR_6$ wherein $R_6$ is a $C_1$–$C_4$ alkyl group, to the locus to be protected.

Still more preferably, the method of the present invention for controlling undesired vegetation comprises applying an effective amount of the compound of formula I wherein $R_1$ is methyl, $R_2$ is trifluoromethyl, $R_3$ is fluorine, chlorine or hydrogen, $R_4$ is chlorine or fluorine, and $R_5$ is hydrogen or $COOR_6$ wherein $R_6$ is isopropyl or cyclopropyl, to the locus to be protected.

Most preferably, the method of the present invention for controlling undesired vegetation comprises applying an effective amount of the compound of formula I wherein $R_1$ is methyl, $R_2$ is trifluoromethyl, $R_3$ is fluorine or hydrogen, $R_4$ is chlorine, and $R_5$ is hydrogen or $COOR_6$ wherein $R_6$ is isopropyl or cyclopropyl, to the locus to be protected.

The herbicidally effective amount of the compound of formula I useful in the method and the composition of this invention depends on a multiplicity of factors such as soil type, soil pH, soil organic matter content, the quantity and intensity of rainfall before and after treatment, air and soil temperature, light intensity and light duration per day. All of these factors have an influence on the efficacy of the compound of this invention.

Preferably, an herbicidally effective amount of the compound of formula I can be from about 0.03 to about 25 pounds of the compound per acre (about 0.033 to about 28 kilograms per hectare), when the compound is employed as a preemergence herbicide. Application of the compound as a preemergence herbicide can typically be made to the soil which contains weeds and the desired crop seed. Such application can be made either to the surface of the soil or incorporated into the upper 1 to 3 inches (2.5 to 7.5 cm.) of soil.

For postemergence herbicidal use, the herbicidally effective amount of the compound can be about 0.03 to about 25 pounds per acres (about 0.033 to about 28 kg/ha). Typically, postemergent application can be accomplished by aerial spraying of the undesired vegetation.

Preferably, the herbicidally effective concentration of the compound of formula I in a composition can be between about 1% to about 95% by weight, based on the total weight of the composition. In an herbicidal emulsion composition, the concentration of the active compound, preferably can be between about 0.002% and about 80% by weight, based on the total weight of the composition.

The present invention also relates to a method for desiccating plants which comprises applying to the plants, a desiccatingly effective amount of the compound of formula I.

The present invention also relates to a method for defoliating plants which comprises applying to the plants, a defoliatingly effective amount of the compound of formula I.

The desiccatingly or defoliatingly effective amount of the compound of formula I in the methods and compositions of this invention will vary depending on a number of factors, including the plant species; the stage of plant development; the method of application; the specific biological effect desired; the air and soil temperature and the quantity and intensity of rainfall before and after treatment; the soil type, pH, fertility and moisture and organic content; the physiological condition and vigor of the target plants; the relative humidity and wind velocity of the air around the crop at the time of treatment; the extent and density of the foliar canopy of the target plant; the light quality, intensity and duration each day; the type and interval of previous and subsequent crop protectant chemical applications. The concentration of the compound of formula I in the desiccant and defoliant compositions of this invention can vary widely, e.g., from about 0.1% to about 95% by weight. Typically the concentration of the compound of formula I in dispersions useful as desiccants and defoliants applied to the soil or foliage, is between about 0.002% and about 80% by weight. The compound of formula I is typically applied as a desiccant or defoliant, at a rate from about 0.01 to about 25 pounds per acre (about 0.011 to 28 kg/ha).

SYNTHESIS

The compound of formula I may be synthesized from a uracil of formula II below, according to the following reaction scheme:

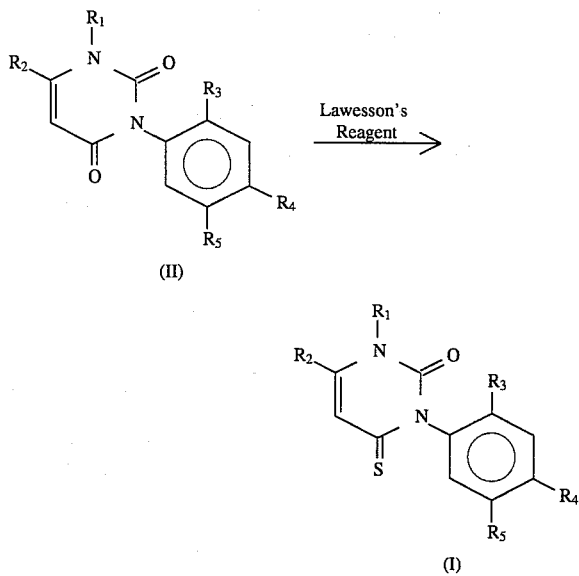

See, e.g., *Advanced Organic Chemistry*, J. March, pp. 893–894 (John Wiley & Sons, New York, 1992) for a description of syntheses using Lawesson's Reagent.

To synthesize the compound of formula II, a compound of the formula

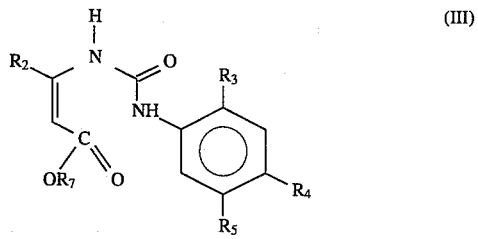

wherein $R_2$ is $C_1$–$C_4$ alkyl or haloalkyl, $R_3$ and $R_4$ are hydrogen or halogen, $R_5$ is hydrogen or $COOR_6$ wherein $R_6$ is $C_1$–$C_4$ linear or branched alkyl, alkenyl, or alkynyl, and $R_7$ is $C_1$–$C_4$ alkyl, is subjected to a base catalyzed cyclization and, if desired, any resulting metal salt form of the uracil derivatives in which $R_1$ is hydrogen, can be converted by treatment with an acid into the corresponding acid form, to produce a compound of the formula

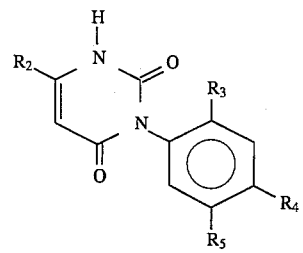

This cyclization can suitably be performed by treating the compound of formula III in an inert, protic organic solvent, such as an alcohol, e.g. methanol, ethanol, or isopropanol; in an inert aprotic organic solvent, such as an aliphatic or cyclic ether, e.g., 1,2-dimethoxyethane, tetrahydrofuran, or dioxan, or in an aromatic compound, e.g., benzene or toluene; in an inert, aprotic polar organic solvent, e.g., dimethylformamide or dimethyl sulfoxide; with such solvents being optionally employed in a two-phase mixture with a hydrocarbon, e.g. n-hexane; or in water, with a base at temperatures between room temperature and the reflux temperature of the reaction mixture. Preferable bases include sodium alcoholates, alkali metal hydroxides such as sodium hydroxide and potassium hydroxide, alkali metal carbonates such as sodium carbonate and potassium carbonate, and sodium hydride. If an alkanol, alkenol, or alkynol is used as a solvent, then the solvent should correspond appropriately to the respective hydroxy compound to obviate undesired competing transesterification reactions. If sodium hydride is used as the base, the solvent is preferably an aliphatic or cyclic ether, dimethylformamide, or dimethyl sulfoxide.

Following completion of the cyclization, the reaction mixture, after exposure to one of the above-mentioned bases or the like, comprises the compound of formula IV in the form of the corresponding alkali metal salt. This compound can be then be isolated and purified from the reaction mixture per se using methods known in the art, or the reaction mixture can be acidified in order to isolate the compound of formula IV itself, using, preferably, an inorganic acid, such as hydrochloric acid, or a strong organic acid, such as an acetic acid or p-toluenesulfonic acid.

The compound of formula IV is then subjected to an alkylation with a corresponding alkylating agent comprising a $C_1$–$C_4$ alkyl group to produce a compound of formula II. "Alkylation" means the introduction of a $C_1$–$C_4$ alkyl group on the unsubstituted nitrogen atom of the compound of formual IV. A $C_1$–$C_4$ alkyl halide, especially the respective chloride or bromide, or sulphate can be used as the alkylating agent.

This alkylation can suitably be performed by treating the compound of formula IV in an inert, protic organic solvent, such as a lower alkanol, e.g. methanol, ethanol, or isopropanol, optionally in mixture with water; in an inert aprotic organic solvent, such as an aliphatic or cyclic ether, e.g., 1,2-dimethoxyethane, tetrahydrofuran, or dioxane; or in an inert, aprotic polar organic solvent, e.g., dimethylformamide or dimethyl sulfoxide, as well as in the presence of a base such as sodium hydride, an alkali metal alcoholate, especially sodium alcoholate, or alkali metal carbonate, especially sodium carbonate, at temperatures between 0° C. and about 50° C., preferably at room temperature. Preferably, the compound of formula IV is first treated with a base such as sodium hydride, ethanolate or carbonate, in the solvent and after a short reaction time is treated with the halide in the solvent. See, e.g., European Patent Application 195,346.

If no particular synthesis is carried out for isolating pure isomers, then the product can be obtained as a mixture of two or more isomers. The isomers can be separated according to methods known in the art. If desired, pure optically active isomers can be prepared, e.g., by synthesis from corresponding optically active starting materials.

The synthesis of the compound of formula III is similarly well known in the art. For example, such compounds can be produced in accordance with the following reaction scheme:

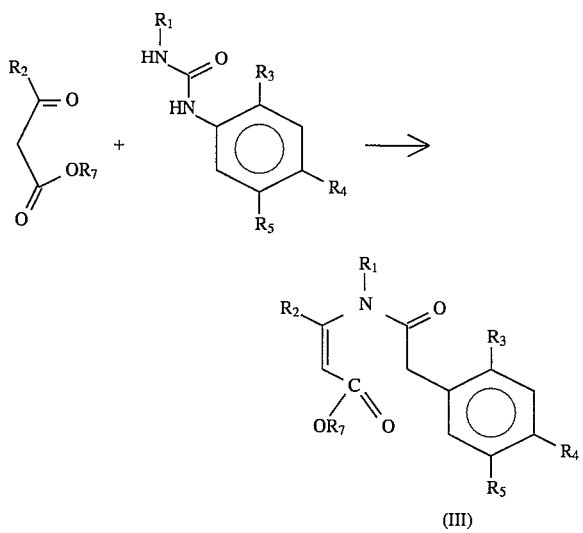

wherein $R^2$, $R^3$, $R^4$, $R^5$, $R^6$ and $R^7$ are as defined above for formula III.

This reaction is typically carried out by reacting the compounds at elevated temperatures in a substantially anhydrous diluent and in the presence of an acid catalyst. Useful diluents include organic solvents that are azeotropic with water, such as aromatic substances, e.g., benzene, toluene, and xylenes; halogenated hydrocarbons, such as methylene chloride, chloroform, carbon tetrachloride, and chlorobenzene; and aliphatic and cyclic ethers, such as 1,2-dimethoxyethane, tetrahydrofuran, and dioxan. Useful acid catalysts include strong inorganic acids, such as sulfuric acid and hydrochloric acid; organic acids, such as p-toluenesulfonic acid; phosphorus-containing acids, such as orthophosphoric acid and polyphosphoric acid; and acid cation exchangers. This reaction is typically conducted in a temperature range of from about 70° C. to 120° C., preferably at the reflux temperature of the reaction mixture. Under these reaction conditions, the desired rapid removal of the water formed in the reaction is accomplished.

The starting materials employed in the reaction scheme to make compounds of formula III are readily obtainable or can be synthesized using methods known in the art.

The following examples are provided to illustrate the present invention.

EXAMPLE 1

Preparation of Ethyl 3-[3,6-dihydro-3-methyl-2- oxo-6-thioxo-4-trifluoromethyl-1-(2H)-pyrimidinyl Benzoate (Compound 5)

A slurry solution of ethyl 3-[3,6-dihydro-2,6-dioxo-3-methyl-4-trifluoromethyl-1 (2H)-pyrimidinyl benzoate (3.7 g, 10.8 mol), Lawesson's reagent [2,4-bis(4-methoxyphenyl)-1,3-dithia-2,4-diphosphetane-2,4-disulfide](4.9 g, 12 mmol), sodium bicarbonate (3.5 g) in 100 ml of toluene, was stirred and refluxed for four hours. Insoluble solid in the slurry solution was then filtered off and the resulting filtrate was then concentrated to an oil. The oil was purified through a short column of aluminum oxide using a 1:1 ether/hexane as eluent to give pure product as a yellow solid with a melting point of 145° C.–146° C.

Yield=2.4 g (62%); Spectroscopic analysis of this compound yielded the following delta values: $^1$H-NMR (CDCl$_3$-60 MHz): 1.36 (t,3H), 3.53 (s,3H), 4.36 (q,2H), 7.03(s,1H), 7.2–8.25 (m,4H).

Elemental analysis for carbon, hydrogen, and nitrogen: % C=50.44; % H=3.74; % N=7.80.

Calculated analyses: % C=50.28; % H=3.66; % N=7.82.

EXAMPLE 2

Preparation of 3, (4-chloropheny)-1,4-dihydro-1-methyl-4-thioxo-6-trifluoromethyl-2(1H)-pyrimidinone (Compound #4)

Using the procedure described in Example 1 and starting with 1-(4-chlorophenyl)-3,6-dihydro-3- methyl-4-trifluoromethyl-2,6-pyrimidinedione the title compound was obtained as a yellow solid with a melting point of 135°–136° C. Spectroscopic analysis of this compound yielded the following delta values: $^1$H-NMR (CDCl$_3$—60 MHz): 3.53(s, 3H), 7.05(s, 1H), 7.15(d, 2H), 7.53 (d,2H)

Elemental analysis for carbon, hydrogen, and nitrogen: % C=44.86; % H=2.49; % N=8.67.

Calculated analyses: % C=44.94; % H=2.51; % N=8.74.

EXAMPLE 3

Preparation of Cyclopropylmethyl 2-Chloro-5-[3,6-dihydro-3-methyl-2-oxo-6-thioxo-4-trifluoro-methyl-1(2H)-pyrimidinyl]Benzoate (Compound #3)

Using the procedure described in Example 1 and starting with cyclopropylmethyl 2-chloro-5-[3,6-dihydro-2,6-dioxo-3-methyl-4-trifluoromethyl-1(2H)-pyrimidinyl]-benzoate, the title compound was obtained as a yellow solid with a melting point of 90°–91° C. Spectroscopic analysis of this compound yielded the following delta values: $^1$H-NMR (CDCl$_3$-60 MHz ): 0.3–1.5 (m, 5H), 3.50 (s,3H), 4.18 (d,2H), 7.03(s,1H), 7.1–7.8(m, 3H).

Elemental analysis for carbon, hydrogen, and nitrogen: % C=48.84; % H=3.41; % N=6.79.

Calculated analyses: % C=48.75; % H=3.37; % N=6.69.

EXAMPLE 4

Preparation of Isopropy 2-chloro-5-[3,6-dihydro-3-methyl-2-oxo-6-thioxo-4-trifluoromethyl-1(2H)-pyrlimidinyl]benzoate (Compound #2)

Using the procedure described in Example 1 and starting with isopropyl 2-chloro-5-[3,6-dihydro-2,6-dioxo- 3-methyl-4-trifluoromethyl-1 (2H)-pyrimidinyl]benzoate, the title compound was obtained as a yellow solid with a melting point of 102°–104° C. Spectroscopic analysis of this sample yielded the following delta values: $^1$H-NMR (CDCl$_3$-60 MHz): 1.35 (d,6H), 3.53 (s,3H), 5.26 (m,1H), 7.06 (s,1H), 7.1–7.8 (m,3H).

Elemental analysis for carbon, hydrogen, and nitrogen: % C=47.50; % H=3.39; % N=6.98.

Calculated analyses: % C=47.24; % H=3.47; % N=6.89.

Preparation of Isopropy 2-chloro-5-[3,6-dihydro-3-methyl-2-oxo-6-thioxo-4-trifluoromethyl-1(2H)-pyrimidinyl]fluorobenzoate (Compound #1)

Using the procedure described in Example 1 and starting with isopropyl 2-chloro-5-[3,6-dihydro-2,6-dioxo-3-methyl-4-trifluoromethyl-1(2H)-pyrimidinyl]-4-fluorobenzoate, the title compound was obtained as a yellow solid with a melting point of 113°–115° C.

Spectroscopic analysis of this compound yielded the following delta values: $^1$H-NMR (CDCl$_3$-60 MHz): 1.36 (d,6H), 3.56 (s,3H), 5.26 (m, 1H), 7.06 (s, 1H), 7.37(d,1H), 7.86(d,1H).

Elemental analysis for carbon, hydrogen, and nitrogen: % C=45.32; % H=3.08; % N=6.61.

Calculated analyses: % C=45.24; % H=3.08; % N=6.60.

TABLE 1

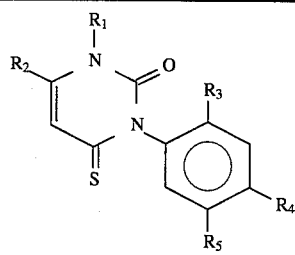

| Cmpd. No. | R$_1$ | R$_2$ | R$_3$ | R$_4$ | R$_5$ | mp (°C.) | $^1$H-NMR (CDCl$_3$, 60 MHz) |
|---|---|---|---|---|---|---|---|
| 1 | CH$_3$ | CF$_3$ | F | Cl | COOCH(CH$_3$)$_2$ | 113–115 | 1.36(d, 3H), 3.56(s, 6H), 5.26(m, 1H), 7.06(s, 1H), 7.37(d, 1h), 7.86(d, 1H) |
| 2 | CH$_3$ | CF$_3$ | H | Cl | COOCH(CH$_3$)$_2$ | 102–104 | 1.35(d, 6H), 3.53(s, 3H), 5.26(m, 1H), 7.06(s, 1H), 7.1–7.8(m, 3H) |
| 3 | CH$_3$ | CF$_3$ | H | Cl | COOCH$_2$—△ | 90–91 | 0.3–1.5(m, 5H), 3.50(s, 3H), 4.18(d, 2H), 7.03(s, 1H), 7.1–7.8(m, 3H) |
| 4 | CH$_3$ | CF$_3$ | H | Cl | H | 135–136 | 3.53(s, 3H, 7.05(s, 1H), 7.15(d, 2H), 7.53(d, 2H) |
| 5 | CH$_3$ | CF$_3$ | H | H | COOCH$_2$CH$_3$ | 145–146 | 1.36(t, 3H), 3.53(s, 3H), 4.36(q, 2H), 7.03(s, 1H), 7.2–8.25(m, 4H) |

EXAMPLE 6

Preemergence Control

The representative compounds of the present invention, tabulated in Table 1, were tested to determine their effectiveness as preemergence herbicides. In this test 300 mg. of each of the compounds tested were dissolved in acetone (10 ml.). Each resulting solution was then stabilized by adding 30 mg. of an emulsifying agent, ethoxylated sorbitan monolaurate (Tween 20™), and 90 ml. of distilled water, to produce stock solutions (3000 ppm). Ten milliliters of each stock solution was then diluted to a concentration of 250 ppm by the addition of distilled water, to produce the test solution/suspension.

The compounds were tested by drenching 46 ml. of each of the test solutions/suspensions, at a rate of 10 pounds per acre (11.2 kg/ha), onto the surface of soil disposed in 4½ inch (11.25 cm)plastic pots in which seeds of the following weeds had been planted: velvetleaf (*Abutilon theophrasti* Medic) (VL), jimsonweed (*Datura stramonium* L.) (JW), or prickly sida (*Sida spinosa* L.) (PS), tall morningglory (*Ipomea purpurea* L. Roth) (TM), switchgrass (*Panicum virgatum* L.) (SG), barnyardgrass (*Echinochloa crus-galli* (L.) Beauv.) (BG), and green foxtail (*Setaria viridis*) (L.) Beauv.) (GF).

Percent control of each of these weeds was determined two weeks after treatment by comparison with untreated controls. The results of these tests are summarized in Table 2. The data in Table 2 demonstrates the herbicidal efficacy exhibited by the representative compounds of this invention.

EXAMPLE 7

Postemergence Control

To illustrate the effectiveness of the compounds of this invention as postemergence herbicides, each stock solution/suspension described in Example 6 was atomized with a conventional DeVilbiss™ sprayer, wetting the foliage of weeds six days after emergence, to the drip point. The rest of the procedure for evaluating postemergence control was identical to the procedure for evaluating preemergence control in Example 6, including the weed species. The percent weed control was evaluated two weeks after treatment. The results of this evaluation are displayed in Table 3.

EXAMPLE, 8

Desiccation Activity

To illustrate the effectiveness of the compounds of this invention as crop plant desiccants, 3000 ppm (mg/1) test solution/suspension of active ingredient was prepared by dissolving 225 mg of each compound to be tested in 2 ml of organic solvent (usually acetone) plus 73 ml of distilled water containing ethoxylated sorbitan monolaurate (Tween 20™) at 0.15% v/v. A 1000 ppm test solution/suspension was produced by further dilution with distilled water. The test solutions/suspensions were applied to soybean [*Glycine max* (L.) Merr. cv. Williams] (3000 ppm) and dry bean (*Phaseolus vulgaris* L. cv. Pinto UI-111) (1000 ppm) plants by atomization with a DeVilbiss™sprayer, wetting the foliage to the drip point. After three weeks in the greenhouse, the plants were scored for leaf desiccation on a 0 to 100 scale, 0 being no damage and 100 being complete kill. The rating system described by Frans and Talber (in Research Methods in Weed Science, 2nd Edition, 1977, Southern Weed Science Society) was used as a guide. The data of this evaluation appear in Table 4.

EXAMPLE 9

Defoliation Activity

To illustrate the effectiveness of the compounds of this invention as crop harvest aids, 1000 ppm (mg/l) test solutions/suspensions of active ingredient were prepared by dissolving 50 mg of each compound in 1 ml of solvent (usually acetone) plus 49 ml of distilled water containing Tween 20™ at 0.15% v/v. Each solution/suspension was then applied to cotton plants (*Gossypium hirsutum* L. cv. Stoneville) by immersing the cotyledons of each plant into the solution/suspension for 5 seconds. After 14 days in the greenhouse, the plants were scored for cotyledon abscission (defoliation) using the following formula:

$$\% \text{ Defoliation} = \frac{\text{Initial Leaf Count} - \text{Final Leaf Count}}{\text{Initial Leaf Count}} \times 100.$$

The data for this evaluation appear in Table 5.

TABLE 2

Preemergence Activity of 10 lb/A (11.2 kg/ha)
Percent Weed control at 11.2 kg/ha

| Cmpd. No. | JW | TM | VL | BG | GF | SG |
|---|---|---|---|---|---|---|
| 1 | 100 | 100 | 100 | 100 | 100 | 100 |
| 2 | 100 | 100 | 100 | 100 | 100 | 100 |
| 3 | 100 | 100 | 100 | 100 | 100 | 100 |
| 4 | 100 | 100 | 100 | 100 | 100 | 100 |
| 5 | 80 | 0 | 90 | 100 | 95 | 100 |

TABLE 3

Postemergence Activity at 3000 ppm
Percent Weed Control at 3000 ppm

| Cmpd. No. | JW | TM | VL | BG | GF | SG |
|---|---|---|---|---|---|---|
| 1 | 100 | 100 | 100 | 100 | 100 | 100 |
| 2 | 100 | 100 | 100 | 100 | 100 | 100 |
| 3 | 100 | 100 | 100 | 100 | 100 | 100 |
| 4 | 100 | 100 | 100 | 100 | 100 | 100 |
| 5 | 100 | 50 | 100 | 90 | 70 | 80 |

TABLE 4

Evaluation of Desiccation Activity
Percent Desiccation

| Compound No. | Soybeans (3000 ppm) | Beans (1000 ppm) |
|---|---|---|
| 1 | 100 | 100 |
| 2 | 100 | 100 |
| 3 | 100 | 100 |
| 4 | 100 | 100 |
| 5 | 40 | 80 |

TABLE 5

Evaluation of Defoliation Activity

| Compound No. | Percent Cotton Defoliation - 14 DAT* |
|---|---|
| 1 | 100 |
| 2 | 100 |
| 3 | 92 |
| 4 | 100 |
| 5 | 17 |

*Days after treatment

What is claimed is:

1. A compound of the formula

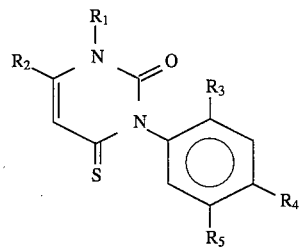

wherein $R_1$ is $C_1$–$C_4$ alkyl, $R_2$ is $C_1$–$C_4$ alkyl or haloalkyl, $R_3$ and $R_4$ are hydrogen or halogen, and $R_5$ is hydrogen or $COOR_6$ wherein $R_6$ is cyclopropyl, cyclopropylmethyl, or $C_1$–$C_8$ linear or branched alkyl, alkenyl, or alkynyl.

2. A compound as recited in claim 1 wherein $R_2$ is $C_1$–$C_4$ fluoroalkyl.

3. A compound as recited in claim 1 wherein $R_1$ is methyl, $R_2$ is trifluoromethyl, $R_3$ is halogen or hydrogen, $R_4$ is halogen, and $R_5$ is hydrogen or $COOR_6$ wherein $R_6$ is a $C_1$–$C_4$ alkyl group.

4. A compound as recited in claim 3 wherein $R_1$ is methyl, $R_2$ is trifluoromethyl, $R_3$ is fluorine or hydrogen, $R_4$ is chlorine, and $R_5$ is hydrogen or $COOR_6$ wherein $R_6$ is isopropyl, cyclopropyl, or cyclopropylmethyl.

5. An herbicidal composition comprising an herbicidally effective amount of a compound as recited in claim 1 and a suitable carrier.

6. An herbicidal composition comprising an herbicidally effective amount of a compound as recited in claim 2 and a suitable carrier.

7. An herbicidal composition comprising an herbicidally effective amount of a compound as recited in claim 3 and a suitable carrier.

8. An herbicidal composition comprising an herbicidally effective amount of a compound as recited in claim 4 and a suitable carrier.

9. A desiccant composition comprising a desiccatingly effective amount of a compound as recited in claim 1 and a suitable carrier.

10. A desiccant composition comprising a desiccatingly effective amount of a compound as recited in claim 2 and a suitable carrier.

11. A desiccant composition comprising a desiccatingly effective amount of a compound as recited in claim 3 and a suitable carrier.

12. A desiccant composition comprising a desiccatingly effective amount of a compound as recited in claim 4 and a suitable carrier.

13. A defoliant composition comprising a defoliatingly effective amount of a compound as recited in claim 1 and a suitable carrier.

14. A defoliant composition comprising a defoliatingly effective amount of a compound as recited in claim 2 and a suitable carrier.

15. A defoliant composition comprising a defoliatingly effective amount of a compound as recited in claim 3 and a suitable carrier.

16. A defoliant composition comprising a defoliatingly effective amount of a compound as recited in claim 4 and a suitable carrier.

17. A method for controlling undesirable vegetation which comprises applying to the locus to be protected an effective amount of a compound as recited in claims 1.

18. A method for controlling undesirable vegetation which comprises applying to the locus to be protected an effective amount of a compound as recited in claims 2.

19. A method for controlling undesirable vegetation which comprises applying to the locus to be protected an effective amount of a compound as recited in claims 3.

20. A method for controlling undesirable vegetation which comprises applying to the locus to be protected an effective amount of a compound as recited in claims 4.

21. A method for desiccating plants which comprises applying to the plants, a desiccatingly effective amount of a compound as recited in claim 1.

22. A method for desiccating plants which comprises applying to the plants, a desiccatingly effective amount of a compound as recited in claim 2.

23. A method for desiccating plants which comprises applying to the plants, a desiccatingly effective amount of a compound as recited in claim 3.

24. A method for desiccating plants which comprises applying to the plants, a desiccatingly effective amount of a compound as recited in claim 4.

25. A method for defoliating plants which comprises applying to the plants, a defoliatingly effective amount of a compound as recited in claim 1.

26. A method for defoliating plants which comprises applying to the plants, a defoliatingly effective amount of a compound as recited in claim 2.

27. A method for defoliating plants which comprises applying to the plants, a defoliatingly effective amount of a compound as recited in claim 3.

28. A method for defoliating plants which comprises applying to the plants, a defoliatingly effective amount of a compound as recited in claim 4.

* * * * *